US006974896B1

(12) United States Patent
Terry et al.

(10) Patent No.: US 6,974,896 B1
(45) Date of Patent: Dec. 13, 2005

(54) TRACE ELEMENT PHYTOREMEDIATION

(75) Inventors: Norman Terry, Berkeley, CA (US); Elizabeth Pilon-Smits, Fort Collins, CO (US); Mark de Souza, Berkeley, CA (US)

(73) Assignee: Regents of the University of California, Oakland, CA (US)

( * ) Notice: Subject to any disclaimer, the term of this patent is extended or adjusted under 35 U.S.C. 154(b) by 0 days.

(21) Appl. No.: 09/365,348

(22) Filed: Jul. 30, 1999

(51) Int. Cl.$^7$ .................. C12N 15/09; C12N 15/82; C12N 15/54; A01H 5/00
(52) U.S. Cl. .................. 800/306; 800/278; 800/298; 435/69.1; 435/193
(58) Field of Search ...................... 800/278, 298, 800/306; 435/468, 69.1, 419, 193; 210/602, 210/681, 682, 688; 75/710

(56) References Cited

U.S. PATENT DOCUMENTS 5,364,451 A * 11/1994 Raskin et al. .................. 75/710
5,785,735 A * 7/1998 Raskin et al. .................. 75/711

FOREIGN PATENT DOCUMENTS

WO    WO 96/32016    * 10/1996
WO    WO 96/ 32016    * 10/1996

OTHER PUBLICATIONS

Bruhl et al. Biochemica et Biophysica Acta vol. 1295, pp. 119-124, Apr. 1996.*
Korch et al. Mol. Gen. Genet vol. 229, pp. 96-108, Mar. 1991.*
Nussbaum et al. Plant Physiol. vol. 88, pp. 1407-1410, Feb. 1988.*
Saito et al. Fed. Eurp. Bioch. Soc. vol. 324(3), pp. 247-252, Jun. 1993.*
Leustek et al. Plant Physiolo. vol. 105, pp. 897-902, 1994.*
Noctor et al. Journal of Exp. Botany, vol. 49, pp. 623-647, Apr. 1998.*
Peter Goldbrough, Metal Tolerance in Plants: The role of Phytochelatins and Metallothioneins. Ann Arbor Press, pp. 221-228, 1999.*
Chaoui et al. Plant Science, vol. 127, pp. 139-147, 1997.*
Terry, N. Improvement of Plants for Selenium and Heavy Metal Phytoremediation Through Genetic Eng. EPRI, TR_14219, Chapter 4.2, 1999.*
Bork et al. "Isolation and Characterization of a gene for assimilatory sulfite reductase from Arabidopsis". GENE (1998), vol. 212(1), pp. 147-153.*
Persson et al. "Se1D homolog from Drosophila Lacking Selenide-dependnet Monoselenophosphate Synthetase Activity". Journal of Molecular Biology (1997), vol. 274(2), pp. 174-178.*
Dahl et al. Adenylylsulfate Reductase from the Sulfate-reducing archaeon Archaeoglobus> Microbiology (1994), vol. 140, pp. 1273-1284.*
Leustek et al. "A cDNA Clone for 5'-Adenylylphosphosulfate Kinase from *Arabidopsis thaliana*". Plant Physiology (1994), vol. 105, pp. 771-772.*
Peck et al. "Cloning of the 3'-phosphoadenylyl sulfate Reductase and Sulfite Reductase Genes from *E.coli* K-12". GENE (1987), vol. 53(2-3), pp. 227-234.*
Hipp et al. "Towards the Phylogony and APS Reductase and Sirohaem Sulfite Reductase in Sulfate-reducing and Sulfur-oxidizing Prokaryotes". Microbiology (1997), vol. 143, pp. 2891-2902.*
Leyh et al. "The Sulfate Activation Locus of *E.coli* K12: Cloning, Genetic, and Enzymatic Characterization". The Journal of Biological Chemistry (1988), vol. 263, pp. 2408-2418.*
Leustek et al. "Cloning of cDNA Encoding ATP Sulfurylase from *Arabidopsis thaliana* ny Functional Expression in *Saccharomyces cerevisiae*". (1994), vol. 105, pp. 897-902.*
Arisi et al. "Response to Cadmium in Leaves of Transformed Poplars Overexpressing Y-glutamycysteine Synthetase". Physiologia Plantarum (2000), vol. 109, pp. 143-149.*
Hatzfed et al. Effect of ATP Sulfurylase Overexpression in Bright Yellow 2 Tobacco Cells. Plant Physiol. (1998), vol. 116, pp. 1307-1313.*
Saito et al. Modulation of Cysteine Biosynthesis in Chloroplasts of Transgenic Tobacco Overexpressing Cysteine synthase[O-Acetylserine(thiol)-lyase. Plant Physiology (1994), vol. 106, pp. 887-895.*
Rudiger Hell. "Molecular Physiology of Plant Sulfur Metabolism". Planta (1997), vol. 202, pp. 138-148.*
Hofgen et al. Manipulation of Thiol Contents in Plants. Amino Acids (2001) 20: 291-299.*
Salt et al. Mechanisms of Cadmium Mobility and Accumulation in Indian Mustard. Plant Physiolo. (1996) 109: 1427-1433.*
Zhu et al. Overexpression of Glutathione Synthase in Indian Mustard Enhances Cadmium Accumulation and Tolerance. Plant Physiology (1999) vol. 119, pp. 73-79.*
Salt et al. Phytoremediation: A Novel Strategy for the Removal of Toxic Metals from the Environment Using Plants. Biotechnology (1995), vol. 12, pp. 466-474.*

(Continued)

Primary Examiner—David T. Fox
Assistant Examiner—Medina A. Ibrahim
(74) Attorney, Agent, or Firm—Richard Aron Osman

(57) ABSTRACT

The invention provides methods and compositions for trace element, particularly heavy metal phytoremediation, including plants which are genetically engineered to overexpress a sulfate assimilation pathway enzyme gene and thereby provide enhanced trace element accumulation. In various embodiments, the plants comprise the gene operably linked to a heterologous promoter, the plant is a member of the Brassicaceae family. In general, the methods comprise the steps of growing such plants in a medium such as soil or water comprising a trace element, under conditions wherein the gene is overexpressed, whereby the plant provides enhanced accumulation of the trace element, whereby the trace element content of the medium is decreased.

19 Claims, No Drawings

OTHER PUBLICATIONS

Guerinot et al. Fortified Foods and Phytoremediation: Two Sides of the Same Coin. Plant Physiology (2001), vol. 125, pp. 164-167.*

Leyh et al. The J. Biol. Chem. (1992), 267(15), pp. 10405-10410.*

Murillo et al. Arch. Biochem. Biophys. (1995) 323: 195-204).*

Logan et al. The Journal of Biological Chemistry (1996), 271:12227-12233.*

Hao Li et al. The Journal of Biological Chemistry (1996), 270 (49): 29453-29459.*

Cherest et al. Mol. Gene. Genet (1987), 210:307-313.*

Rosenthal et al. GENE (1995) 165:243-248.*

Klonus et al. Plant J. (1994) 6:105-112.*

Kurima et al. The Journal of Biological Chemistry (1999), 274 (47): 33306-33312.).*

Persson et al. Journal of Molecular Biology (1997), vol. 274, pp. 174-180.*

Tormay et al. Eur. J. Biochem (1998), vol. 254, pp. 655-661.*

Delhaize et al. Plant Physiology (1989), vol. 89, pp. 700-706.*

Knecht et al. New Phytol. (1992), vol. 122, pp. 681-688.*

Hesse et al. Plant Physiology (1995), vol. 108, pp. 851-852.*

Jain et al. Plant Physiology (1994), vol. 105, pp. 771-772.*

* cited by examiner

TRACE ELEMENT PHYTOREMEDIATION

FIELD OF THE INVENTION

The field of the invention is enhanced trace element, particularly heavy metal phytoremediation by genetically engineered plants with respect to sulfur assimilation.

BACKGROUND OF THE INVENTION

Heavy metals and metalloids such as cadmium, lead and mercury are an increasing environmental problem worldwide. Green plants can be used to remove heavy metals by sequestrating, stabilizing or biochemically transforming them. This cost-effective and environment-friendly technology has been called phytoremediation. Hyperaccumulators—heavy metal accumulating flora collected from metal-contaminated sites—offer one option for the phytoremediation of metal-contaminated sites. However, these hyperaccumulators tend to grow slowly and produce little biomass. An alternative approach is to genetically engineer fast-growing species to improve their metal tolerance and metal accumulating capacity.

Selenium (Se) is an essential trace element for animals and bacteria, but is also toxic at higher concentrations. Selenium is naturally present in soils derived from shale rock (up to ~100 ppm) and when these soils are irrigated, selenate ($SeO_4^{2-}$) leaches into the drainage water. In addition, selenite ($SeO_3^{2-}$) is a common contaminant in oil refinery wastewater. Plants can take up Se from water, soil or sediment, accumulate it in their tissues, and volatilize it. Volatile forms of Se, such as dimethylselenide (DMSe), have been reported to be 500–600 times less toxic compared to inorganic forms of Se. For Se phytoremediation, terrestrial plants can be grown in Se-contaminated soils, and aquatic plants can be grown in constructed wetlands used for the treatment of Se-contaminated wastewater. The uptake and assimilation of selenate and sulfate are generally assumed to follow the same pathway. Sulfate is actively transported into plant cells by sulfate permease. For reduction, sulfate is first activated by ATP sulfurylase to form adenosine phospho sulfate, which is subsequently reduced to free sulfite by APS reductase. ATP sulfurylase, similar to sulfate permease, was induced by sulfur starvation and repressed by feeding sulfate or reduced forms of S. Here we show that overexpresssion in plants of genes in the sulfate assimilation pathway provides enhanced selenate reduction, Se accumulation and Se tolerance.

We also disclose the surprising finding that overexpression of these genes also enhances heavy metal tolerance and accumulation, and describe fast-growing plants with superior heavy metal accumulation and tolerance for phytoremediation. These transgenic plants overexpressing eznymes from the sulfate assimilation pathway (engineered sulfate assimilator plants) greatly enhance the efficiency of heavy metal phytoextraction from polluted soils and wastewater.

Relevant Literature

See, Pilon-Smits et al., 1999, Plant Physiol 119, 123–32, and references cited therein.

SUMMARY OF THE INVENTION

The invention provides methods and compositions for trace element, particularly heavy metal phytoremediation. The subject compositions include plants which are genetically engineered to overexpress a sulfate assimilation pathway enzyme gene selected from: (a) Sulfate permease; (b) 2.7.7.4 Sulfate adenylyltransferase; ATP sulfurylase; Sulfurylase; (c) 2.7.1.25 Adenylylsulfate kinase; (d) 1.8.99.2 Adenylylsulfate reductase; (e) 1.8.1.2 Sulfite reductase (NADPH); (f) 1.8.7.1 Sulfite reductase (ferredoxin); (g) 1.8.99.1 Sulfite reductase; (h) 2.7.9.3 Selenide, water dikinase; selenidephosphate synthase; (i) 2.9.1.1 L-Seryl-tRNA (Ser) seleniumtransferase; Selenocysteinyl-tRNA (Ser) synthase; Selenocysteine synthase; and (j) 4.2.99.8 Cysteine synthase; O-Acetylserine (thiol)-lyase; O-Acetylserine sulfhydrylase; and thereby provide enhanced trace element, particularly heavy metal accumulation. In particular embodiments, the plants comprise the gene operably linked to a heterologous promoter, the plant is a member of the Brassicaceae family, such as *Brassica juncea*, and/or the trace element is selected from cadmium, mercury, chromium, molybdenum, tungsten and uranium. In general, the subject methods comprise the steps of growing such plants in a medium such as soil or water comprising a targeted trace element, particularly a targeted heavy metal, under conditions wherein the sulfate assimilation gene is overexpressed, whereby the plant provides enhanced assimilation of the trace element, whereby the trace element content of the medium is decreased.

DESCRIPTION OF PARTICULAR EMBODIMENTS OF THE INVENTION

The following descriptions of particular embodiments and examples are offered by way of illustration and not by way of limitation. Unless contraindicated or noted otherwise, in these descriptions and throughout this specification, the terms "a" and "an" mean one or more, the term "or" means and/or and polynucleotide sequences are understood to encompass opposite strands as well as alternative backbones described herein.

The subject compositions include plants which are genetically engineered to overexpress a sulfate assimilation gene and thereby provide enhanced trace element, particularly heavy metal accumulation. A wide variety of plants may be used, as urged by the particular trace element, medium, site geology, topology, weather, etc. Additional factors for selection include large biomass production, relatively high trace element accumulation capacity, and ease of genetic engineerability (Zhu et al., 1999, Plant Physiol 119:73–79). Suitable plants are readily screened for requisite engineerability and expression from examplars of candidate plant varieties by those skilled in the art of plant genetic engineering, as exemplified below. Suitable plants source materials include commercially available varieties of Acanthaceae, Aceraceae, Acoraceae, Adiantaceae, Agavaceae, Aizoaceae, Alismataceae, Alliaceae, Aloeaceae, Alstroemeriaceae, Amaranthaceae, Amaryllidaceae, Anacardiaceae, Anemiaceae, Angiopteridaceae, Annonaceae, Apocynaceae, Aponogetonaceae, Aquifoliaceaei, Araceae, Araliaceaei, Araucariaceae, Arecaceae, Aristolochiaceae, Asparagaceae, Aspleniaceae, Asteliaceae, Asteraceae, Balsaminaceae, Basellaceae, Bataceae, Begoniaceae, Berberidaceae, Betulaceae, Bignoniaceae, Bixaceae, Blechnaceae, Bombacaceae, Boraginaceae, Brassicaceae: *Alliaria petiolata, Arabidopsis thaliana, Arabis petiolaris, Arabis pumila, Arabis* sp., *Berteroa incana, Biscutella laevigata, Brassica junceae, Brassica napus, Brassica napus* var. *napus, Brassica nigra, Brassica oleracea, Brassica oleracea* var. *gongylo, Capsella bursa-pastoris, Cardamine pratensis, Cochlearia officinalis, Dentaria laciniata, Descurainia pinnata, Draba asprella, Draba verna, Draba, Erysimum aspe-* rum, *Erysimum asperum, Erysimum capitatum, Lepidium flavum, Lepidium virginicum, Lesquerella argyraea, Lesquerella densiflora, Lesquerella rubicundula, Lesquerella* sp., *Lobularia maritima, Lunaria annua, Lunaria rediviva, Neobeckia aquatica, Nerisyrenia camporum, Physaria chambersii, Raphanus sativus, Sinapis alba, Stanleya pinnata, Streptanthus cordatus, Thlaspi arvense, Thlaspi rotundifolium*, Bromeliaceae, Buddlejaceae, Burseraceae, Buxaceae, Cabombaceae, Cactaceae, Caesalpiniaceae, Callitrichaceae, Calochortaceae, Calyceraceae, Campanulaceae, Cannabaceae, Cannaceae, Capparaceae, Caprifoliaceae, Caricaceae, Caryophylaceae, Casuarinaceae, Celastraceae, Chenopodiaceae, Cistaceae, Clusiaceae, Cneoraceae, Cochlospermaceae, Combretaceae, Commelinaceae, Convallariaceae, Convolvulaceae, Comaceae, Corylaceae, Crassulaceae, Crossosomataceae, Cucurbitaceae, Cunoniaceae, Cupressaceae, Cuscutaceae, Cyatheaceae, Cycadaceae, Cyperaceae, Cyrillaceae, Dennstaedtiaceae, Dicksoniaceae, Didiereaceae, Dilleniaceae, Dioscoreaceae, Dipsacaceae, Dipterocarpaceae, Droseraceae, Dryopteridaceae, Ebenaceae, Ehretiaceae, Elaeagnaceae, Elaeocarpaceae, Elatinaceae, Empetraceae, Epacridaceae, Ephedraceae, Equisetaceae, Ericaceae, Eriocaulaceae, Erythroxylaceae, Escalloniaceae, Euphorbiaceae, Eupomatiaceae, Fabaceae, Fagaceae, Flacourtiaceae, Fouquieriaceae, Frankeniaceae, Fumariaceae, Gentianaceae, Geraniaceae, Gesneriaceae, Ginkgoaceae, Globulariaceae, Goodeniaceae, Grossulariaceae, Gunneraceae, Haemodoraceae, Haloragaceae, Hamamelidaceae, Heliconiaceae, Hippocastanaceae, Hyacinthaceae, Hydrangeaceae, Hydrophyllaceae, Hypericaceae, Iridaceae, Isoetaceae, Juglandaceae, Juncaceae, Koeberliniaceae, Krameriaceae, Lamiaceae, Lauraceae, Lecythidaceae, Lemnaceae, Lentibulariaceae, Liliaceae, Limnanthaceae, Limnocharitaceae, Linaceae, Loasaceae, Lobeliaceae, Loganiaceae, Lomandraceae, Lomariopsidaceae, Loranthaceae, Lycopodiaceae, Lythraceae, Magnoliaceae, Malpighiaceae, Malvaceae, Marantaceae, Marcgraviaceae, Marsileaceae, Martyniaceae, Mayacaceae, Melanthiaceae, Melastomataceae, Meliaceae, Melianthaceae, Menispermaceae, Menyanthaceae, Mimosaceae, Monimiaceae, Monotropaceae, Moraceae, Musaceae, Myoporaceae, Myricaceae, Myristicaceae, Myrsinaceae, Myrtaceae, Nelumbonaceae, Nyctaginaceae, Nymphaeaceae, Nyssaceae, Ochnaceae, Oenotheraceae, Oleaceae, Oliniaceae, Onagraceae, Ophioglossaceae, Orchidaceae, Orobanchaceae, Osmundaceae, Oxalidaceae, Paeoniaceae, Pandanaceae, Papaveraceae, Passifloraceae, Pedaliaceae, Philydraceae, Phormiaceae, Phytolaccaceae, Pinaceae, Piperaceae, Pittosporaceae, plantaginaceae, Platanaceae, Plumbaginaceae, Poaceae, Podocarpaceae, Podophyllaceae, Polemoniaceae, Polygalaceae, Polygonaceae, Polypodiaceae, Pontederiaceae, Portulacaceae, Primulaceae, Proteaceae, Pteridaceae, Punicaceae, Pyrolaceae, Raffiesiaceae, Ranunculaceae, Resedaceae, Restionaceae, Rhamnaceae, Rosaceae, Rubiaceae, Ruscaceae, Rutaceae, Salicaceae, Salviniaceae, Santalaceae, Sapindaceae, Sapotaceae, Sarraceniaceae, Saururaceae, Saxifragaceae, Scrophulariaceae, Selaginellaceae, Simaroubaceae, Smilacaceae, Solanaceae, Sparganiaceae, Sterculiaceae, Strelitziaceae, Styracaceae, Taccaceae, Tamaricaceae, Taxaceae, Taxodiaceae, Theaceae, Thelypteridaceae, Thymelaeaceae, Tiliaceae, Trapaceae, Tremandraceae, Trilliaceae, Trochodendraceae, Tropaeolaceae, Tumeraceae, Typhaceae, Uhnaceae, Urticaceae, Valerianaceae, Verbenaceae, Veronicaceae, Violaceae, Viscaceae, Vitaceae, Welwitschiaceae, Winteraceae, Xanthorrhoeaceae, Xerophyllaceae, Xyridaceae, Zamiaceae, Zingiberaceae, and Zygophyllaceae. Preferred plant species include members of the Salicaceae family, such as *Populus angustifolia*; the Solanaceae family, such as *Nicotiana tabacum*; the Caryophyllaceae family, such as *Silene cucubalis*; and the Brassicaceae family, such as *Brassica juncea*.

In particular embodiments, the plants comprise a gene encoding an enzyme of the sulfate assimilation pathway operably linked to a heterologous promoter. A wide variety of sulfate assimilation genes are known in the art or readily isolated from target cells, including plant, microbial and animal sources, preferably from *Arabidopsis thaliana*; preferred genes are itemized in Table 1, preceded by their corresponding EC number.

TABLE 1

Exemplary sulfate assimilation genes.

| E.C. Number | Functional Name | Cloned Species |
|---|---|---|
| 3.1.6.1 | Sulfate permease | ECO, HSA |
| 2.7.7.4 | Sulfate adenylyltransferase; ATP sulfurylase; Sulfurylase | ECO, BSU, |
| 2.7.1.25 | Adenylylsulfate kinase | ECO, BSU, SYN, AFU, APE, SCE |
| 1.8.99.2 | Adenylylsulfate reductase | AFU |
| 1.8.1.2 | Sulfite reductase (NADPH) | ECO, BSU, CTR, CPN, AFU, SCE |
| 1.8.7.1 | Sulfite reductase (ferredoxin) | SYN, MTH |
| 1.8.99.1 | Sulfite reductase | AFU, Desulfovibrio vulgaris, Desulfovibrio simplex, PIS |
| 2.7.9.3 | Selenide, water dikinase; selenidephosphate synthase | ECO, HIN, AAE |
| 2.9.1.1 | L-Seryl-tRNA (Ser) seleniumtransferase; Selenocysteinyl-tRNA (Ser) synthase; Selenocysteine synthase | ECO, HIN, HPY, HPJ, AAE |
| 4.2.99.8 | Cysteine synthase; O-Acetylserine (thiol)-lyase; O-Acetylserine sulfhydrylase | ECO, HIN, HPY, HPJ, BSU, MTU, SYN, AAE, TMA, APE, SCE, CEL |

Legend for Cloned Species of Table 1.
ECO = *Escherichia coli*
BSU = *Bacillus subtilis*
HSA = *Homo sapiens*
SYN = *Synechocystis sp.*
AFU = *Archaeoglobus fulgidus*
APE = *Aeropyrum pernix*
SCE = *Saccharomyces cereviseae*
CTR = *Chlamydia trachomatis*
CPN = *Chlamydia pneumoniae*
MTH = *Methanobacterium thermoautotrophicum*
HIN = *Haempphilus influenzae*
AAE = *Aquiflex aeolicus*
HPY = *Helicobacter pylori* 26695
HPJ = *Helicobacter pylori* J99
MTU = *Mycobacterium tuberculosis*
TMA = *Thermotoga maritima*
CEL = *Caenorhabditis elegans*
PIS = *Pyrobaculum islandicum*

The precise nature of the recombinant expression construct is not essential so long as the requisite expression and associated trace element accumulation increase is effected. For example, in a particular embodiment, the *Arabidopsis* ATP sulfurylase gene, fused to an Arabidopsis chloroplast transit sequence and driven by the double-enhanced 35S CaMV promoter. Other suitable promoter examples include the nos promoter, 35S—35S, and 35S with the AMV leader sequence. The construct may also comprise additional elements, such as a selectable marker. For example, in a particular embodiment, the construct contains the nptII gene, which confers kanamycin resistance. Transformations, plant cultures and analyses are readily carried out by those skilled in the art, as exemplified below.

The subject plants and methods are amenable to accumulating a wide variety of trace element, particularly metalloids and heavy metals, wherein the applicability to any target element is readily determined empirically, as in the methods described herein. In particular embodiments, the trace element is selected from cadmium, lead, tungsten, uranium, barium, copper, manganese, nickel, vanadium, zinc, chromium, iron, cobalt, gold, silver, mercury tin, molybdenum, beryllium, boron, arsenic, selenium, polonium and tellurium; preferably metals of common site contamination and with relatively high human or environmental toxicity, such as cadmium, mercury and chromium.

80%, more preferably at least 200% greater than an otherwise comparable unengineered plant.

Table 2 shows exemplary transformed plant species demonstrating enhanced trace element assimilation and/or accumulation over wild-type counterparts, as described below.

Table 2. Exemplary plant species demonstrating enhanced elemental assimilation in wild-type plants (wt) and the corresponding plant overexpressing recombinant sulfate assimilation enzyme gene (r); experimental material and methods substantially as described below. SA gene provides encoded enzyme EC number.

| Plant Species | SA gene | Promoter | Element | Medium | wt | r |
|---|---|---|---|---|---|---|
| Brassica juncea | 2.7.7.4 | 35S CaMV | Cd | hydroponic | +/− | +++ |
| Brassica juncea | 2.7.7.4 | 35S CaMV | Mo | hydroponic | +/− | +++ |
| Brassica juncea | 2.7.7.4 | 35S CaMV | W | hydroponic | +/− | +++ |
| Brassica juncea | 2.7.7.4 | 35S CaMV | Te | hydroponic | +/− | +++ |
| Brassica juncea | 2.7.7.4 | 35S CaMV | U | hydroponic | +/− | +++ |
| Brassica juncea | 2.7.7.4 | 35S CaMV | Hg | hydroponic | +/− | +++ |
| Brassica juncea | 2.7.7.4 | 35S CaMV | Se | hydroponic | +/− | +++ |
| Brassica juncea | 3.1.6.1 | 35S CaMV | Cd | hydroponic | +/− | +++ |
| Brassica juncea | 3.1.6.1 | 35S CaMV | Mo | hydroponic | +/− | +++ |
| Brassica juncea | 3.1.6.1 | 35S CaMV | W | hydroponic | +/− | +++ |
| Brassica juncea | 3.1.6.1 | 35S CaMV | Te | hydroponic | +/− | +++ |
| Brassica juncea | 3.1.6.1 | 35S CaMV | U | hydroponic | +/− | +++ |
| Brassica juncea | 3.1.6.1 | 35S CaMV | Hg | hydroponic | +/− | +++ |
| Brassica juncea | 3.1.6.1 | 35S CaMV | Se | hydroponic | +/− | +++ |
| Brassica juncea | 2.7.1.25 | 35S CaMV | Cd | hydroponic | +/− | +++ |
| Brassica juncea | 1.8.99.2 | 35S CaMV | Cd | hydroponic | +/− | +++ |
| Brassica juncea | 1.8.1.2 | 35S CaMV | Cd | hydroponic | +/− | +++ |
| Brassica juncea | 1.8.7.1 | 35S CaMV | Cd | hydroponic | +/− | +++ |
| Brassica juncea | 1.8.99.1 | 35S CaMV | Cd | hydroponic | +/− | +++ |
| Brassica juncea | 2.7.9.3 | 35S CaMV | Cd | hydroponic | +/− | +++ |
| Brassica juncea | 2.9.1.1 | 35S CaMV | Cd | hydroponic | +/− | +++ |
| Brassica juncea | 4.2.99.8 | 35S CaMV | Cd | hydroponic | +/− | +++ |
| Brassica juncea | 2.7.7.4 | nos | Cd | hydroponic | +/− | +++ |
| Brassica juncea | 2.7.7.4 | 35S-35S | Cd | hydroponic | +/− | +++ |
| Brassica juncea | 2.7.7.4 | 35S -AMV | Cd | hydroponic | +/− | +++ |
| Populus angustifolia | 2.7.7.4 | 35S CaMV | Cd | hydroponic | +/− | +++ |
| Nicotiana tabacum | 2.7.7.4 | 35S CaMV | Cd | hydroponic | +/− | +++ |
| Silene cucubalis | 2.7.7.4 | 35S CaMV | Cd | hydroponic | +/− | +++ |
| Brassica juncea | 2.7.7.4 | 35SCaMV | Cd | loamy soil | +/− | +++ |
| Populus angustifolia | 2.7.7.4 | 35S CaMV | Cd | loamy soil | +/− | +++ |
| Nicotiana tabacum | 2.7.7.4 | 35S CaMV | Cd | loamy soil | +/− | +++ |
| Silene cucubalis | 2.7.7.4 | 35S CaMV | Cd | loamy soil | +/− | +++ |
| Brassica juncea | 2.7.7.4 | 35S CaMV | Cd | sandy soil | +/− | +++ |
| Populus angustifolia | 2.7.7.4 | 35S CaMV | Cd | sandy soil | +/− | +++ |
| Nicotiana tabacum | 2.7.7.4 | 35S CaMV | Cd | sandy soil | +/− | +++ |
| Silene cucubalis | 2.7.7.4 | 35S CaMV | Cd | sandy soil | +/− | +++ |
| Brassica juncea | 2.7.7.4 | 35S CaMV | Cd | clay soil | +/− | +++ |
| Populus angustifolia | 2.7.7.4 | 35S CaMV | Cd | clay soil | +/− | +++ |
| Nicotiana tabacum | 2.7.7.4 | 35S CaMV | Cd | clay soil | +/− | +++ |
| Silene cucubalis | 2.7.7.4 | 35S CaMV | Cd | clay soil | +/− | +++ |

In general, the subject methods comprise the steps of (a) identifying a medium such as soil or water as containing an excessive amount of a trace element, particularly a heavy metal; and (b) growing such plants in the medium, under conditions wherein the sulfate assimilation gene is overexpressed, whereby the plant provides enhanced accumulation of the trace element, whereby the trace element content of the medium is decreased. The decrease may be measured directly or indirectly, as accumulation in the plants. In particular embodiments, the decrease is measured as enhanced accumulation of at least 50%, preferably at least

EXPERIMENTAL PROTOCOLS AND RESULTS FOR EXEMPLARY EMBODIMENTS

Plant transformation and characterization. B. juncea seeds (Indian mustard, accession no. 173874), were obtained from the North Central Regional Plant Introduction Station, Ames, Iowa. The DNA construct used to transform the plants contained the A. thaliana APSI cDNA including its own chloroplast transit sequence, under the control of the CaMV 35S promoter (Chen et al., 1997, Physiol Plant 101:165–172). A 1490 bp XhoI-Psp1406I fragment from pYES-APS 1 (Leustek et al., 1994, Plant Physiol 105: 897–902) was cloned into the BamHI-AccI sites of pBluescriptSK(+). Then the polylinker restriction sites from pBluescript, SpeI and KpnI, were used to clone APSI into pFF20. PFF20 is a modified form of pFF19 (Timmermans et al., 1990, J Biotechnol 14:333–344). pFF19 was modified by replacing the HindIII site with a SalI site and by eliminating the SalI site from the polylinker of the plasmid. The expression cassette from pFF20 carrying APS1 was cloned as an EcoRI-SalI fragment into the EcoRI and SalI sites of pBI101.

This construct was used to transform *Agrobacterium tumefaciens* strain C53C1 as follows. All in vitro plant tissue cultures were grown at 25° C., under continuous light. For transformation, *B. juncea* hypocotyl segments were isolated from 3-day old, axenically-grown seedlings (200–300 seedlings per transformation). The segments were immersed for 1 h in a suspension of the APS1-containing *A. tumefaciens* strain ($OD_{600}$=0.6, suspended in Murashige and Skoog medium); the bacteria were previously grown for 3 d at 28° C. in liquid LB medium in the presence of 200 $\mu$M acetosyringone (3,5-dimethoxy-4-hydroxy-acetophenone, Fluka). After immersion in the bacteria suspension, the hypocotyls were blotted dry and transferred to modified Murashige and Skoog (MS) medium, containing MS salts and vitamins (Sigma, M5519), 4 g $L^{-1}$ agarose, 10 g $L^{-1}$ of each sucrose, glucose and mannitol, 200 $\mu$M acetosyringone, 2 mg $L^{-1}$ BAP and 0.1 mg $L^{-1}$ NAA. After 2 days of cocultivation the hypocotyls were washed for 45 min in standard liquid MS medium, blotted dry, and transferred to medium containing MS salts and vitamins, 4 g $L^{-1}$ agarose, 10 g $L^{-1}$ of sucrose, glucose and mannitol, 200 mg $L^{-1}$ cefotaxime, 100 mg $L^{-1}$ vancomycin, 20 mg $L^{-1}$ kanamycin, 2 mg $L^{-1}$ BAP, 0.1 mg $L^{-1}$ NAA, and 30 $\mu$M $AgNO_3$. After 11 days the hypocotyls were transferred to the same medium containing 10% coconut water (Sigma). Established shoots were transferred to standard MS medium containing 30 g $L^{-1}$ sucrose, 100 mg $L^{-1}$ cefotaxime and 1 mg $L^{-1}$ IBA to induce root formation. PCR was used to identify APS transgenic lines among the kanamycin-resistant lines obtained.

Total RNA was isolated from 7 d old seedling shoots using the RNeasy Plant Mini Kit, according to the manufacturer's instructions (Qiagen). RNA electrophoresis, Northern blot hybridization and washing of blots were performed as described by Hwang and Herrin (1994, Plant Mol Biol 26:557–569). The RNA blots were stained with methylene blue to check for equal loading and transfer (Herrin and Schmidt, 1988, BioTechniques 6:196–200). The APS1 DNA probe was generated by PCR using the primers described above. The PCR product was purified from the agarose gel and labelled with $^{32}$P-dCTP using random priming (Feinberg and Vogelstein, 1983, Anal Biochem 132:6–13).

Leaf and root samples for ATP sulfurylase enzyme analysis were collected from 9 day old seedlings and from 6-week old mature plants, all grown under greenhouse conditions. The samples, which consisted of total shoots/roots from seedlings, or pooled samples from all leaves of a plant, were immediately stored on dry ice, ground in liquid nitrogen, and extracted with 1 ml $g^{-1}$ fresh weight of a buffer containing 50 mM Tris pH8, 20% glycerol, 2 mM EDTA and 0.1 mM phenylmethylsulfonylfluoride (PMSF). ATP sulfurylase enzyme activity was assayed in the reverse reaction, according to Renosto et al. (1991, Arch Biochem Biophys 290: 66–78).

Selenium tolerance and accumulation experiments. To test the Se tolerance of seedlings, T2 seeds from APS plants and wildtype *B. juncea* seeds were sterilized by rinsing them in 96% ethanol for 30 seconds, then in 0.65% hypochlorite solution for 30 minutes, and subsequently in sterile deionized water for 5×10 minutes, all on a rocking platform. Fifty sterilized seeds were sown in a grid system in Magenta boxes (Sigma) on half-strength MS medium with 10 g.$L^{-1}$ sucrose, and 5 g $L^{-1}$ phytagar (Sigma), with or without added selenate (400 $\mu$M). After 7 days at 25° C. under continuous light, individual seedlings were harvested, washed, weighed and the root length was measured.

For analysis of Se accumulation and tolerance in mature plants, APS and wildtype *B. juncea* plants were grown in 4" pots containing coarse sand. The pots were maintained in a greenhouse with controlled temperature (24° C.) and a short-day (9 h) photoperiod, to prevent them from flowering. The plants were watered twice a day, once with tap water and once with 0.5 strength Hoagland's solution (Hoagland and Arnon, 1938, CA Agricultural Experiment Station Circulation 347:1–39).

One week before the Se treatment, when the plants were 4–6 weeks old, the plants were gently washed in water to remove the sand adhering to the roots and transferred into plastic boxes containing 3.5 L hydroponic solution (0.125 strength Hoagland's solution), which was aerated. After one week in hydroponics, the nutrient solution was replaced by fresh solution containing various concentrations of selenium. After 8 d of Se treatment, the plants were harvested and weighed. For elemental analysis, the plants were thoroughly washed in running de-ionized water to remove any Se that was bound to the outside of the roots, dried at 70° C., and the roots and shoots were ground separately using a mortar and pestle.

Biochemical analysis of transgenic plants. For elemental analysis, powdered plant tissues (100 mg dry weight samples) were acid-digested according to Martin (1975, Atomic Abs Newslett 14:109–116). Selenium concentrations were analyzed in the acid digests using atomic absorption spectroscopy in combination with hydride generation (Mikkelsen, 1987). Sulfur concentrations in the acid digests were analyzed by Inductively-Coupled Plasma Atomic Emission Spectroscopy (ICP-AES) according to Fassel (1978, Science 202:183–191).

The non-protein thiol content of plant extracts was measured photospectrometrically according to Galli et al. (1996, Planta 198:139–143). Extracts were prepared from 100 mg homogenized shoot samples by adding 300 ml of a solution containing 1M NaOH and 1 mg $L^{-1}$ $NaBH_4$. The homogenate was centrifuged for 3 min at 13,000×g at 4° C. 300 ml of the supernatant was acidified by addition of 50 ml 37% HCl, and 20 $\mu$L of this solution was added to 1 mL of of 5,5'-dithiobis(2-nitrobenzoic acid), (Ellman's reagent, Ellman, 1959, Arch Biochem Biophys 82:70–77); the absorption was measured at 412 nm.

Total glutathione was measured according to a modification of the method described by Hermsen et al. (1997, Plant Physiol Biochem 35:491–496). Plant samples were ground in liquid nitrogen, and 100 mg of plant tissue was extracted with 0.3 mL of a solution containing 0.1M HCl and 1 mM EDTA. 150 $\mu$L of extract was then mixed with 300 $\mu$L 0.1M phosphate buffer (pH 8.0) containing 2.4 mM DTE and 45 $\mu$L 0.28 M NaOH. This mixture was incubated for 1 h at room temperature. After 1 min of centrifugation, 400 $\mu$L of supernatant was transferred to a new tube and 533 $\mu$L of phosphate buffer (pH 6.2) was added, followed by 26.7 $\mu$L of 1-chloro-2,4-dinitrobenzene. The $OD_{340}$ of this solution was set at 0, after which 0.72 U of glutathione S-transferase was added and the change in $OD_{340}$ was measured continuously over 4 min.

Trace element plant growth and tolerance experiments. Seedling experiments: T2 seeds from transgenic lines and wild type Indian mustard were sterilized by rinsing them in 95% ethanol for 30 seconds, then in 1% hypochlorite solution for 30 minutes, and subsequently in sterile deionized water for five times, 10 minutes each time, all on a rocking platform. Fifty sterilized seeds were sown in a grid pattern in Magenta boxes (Sigma) on half-strength MS medium containing 10 g L$^{-1}$ sucrose, 5 g L$^{-1}$ phytagar (Sigma), and different concentrations of CdSO$_4$ (0, 0.15, 0.20, or 0.25 mM). After 7 days at 25° C. under continuous light, the individual seedlings were harvested, washed, weighed and the length of the longest root was measured.

Mature plant experiments: Seeds of transgenic and wild type Indian mustard were sterilized and sown in Magenta boxes as described above. After 5 days on agar the seedlings were transferred to 4" pots containing coarse sand. The pots were maintained in a greenhouse with controlled temperature (24° C.) and a short-day (9 h) photoperiod (to prevent them from flowering). The plants were watered twice a day, once with tap water and once with 0.5 strength Hoagland's solution. After 6 weeks of growth under these conditions, the plants were gently washed in water to remove the sand adhering to the roots and transferred to a nutrient film technique (NFT) setup (Zayed, 1987, Influence of sodium chloride on ion uptake and yield of tomatoes and lettuce grown by hydroponics. Ph.D. Thesis. Wye College, University of London). Briefly, the plants were placed in channels and quarter-strength Hoagland's nutrient solution (Hoagland and Arnon, 1938) amended with 0.05, 0.075 and 0.1 mM Cd (as CdSO$_4$) was circulated along the plant roots. The NFT setup was maintained under the same greenhouse conditions as described earlier. Plants were harvested after 14 d and thoroughly washed under running deionized water to remove any trace elements adhering to the tissue. Total fresh weights of the plants were measured before and after the experiment to determine the effect of different concentrations of Cd on growth. Shoot and root tissues were separated and dried at 70° C. for 3 days. The dried tissues were weighed and then ground in a Wiley mill.

Results. APS lines showed no phenotypic differences compared to untransformed *B. juncea* plants. The APS plants showed at least 2-fold higher ATP-sulfurylase activity in their shoots, roots and leaves compared to wildtype plants and seedlings. Both seedlings and mature APS plants showed increased Se tolerance and accumulation. In addition, APS plants showed increased sulfate reduction, as measured by reduced sulfer compounds glutathione and total thiol. APS plants showed improved Cd accumulation and tolerance, higher levels of GSH and NPTs.

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for decreasing the trace element content of a medium, comprising the steps of:
   (a) identifying a medium as containing an excessive amount of a heavy metal trace element; and
   (b) growing in the medium a plant of the Brassicaceae family which is transformed with a nucleic acid encoding the sulfate assimilation pathway enzyme E.C. 2.7.7.4 Sulfate adenylyltransferase under conditions wherein the sulfate assimilation pathway enzyme is overexpressed; whereby the transformed plant provides enhanced accumulation of the trace element, whereby the trace element content of the medium is decreased.

2. The method according to claim 1, wherein the nucleic acid is operably linked to a heterologous promoter.

3. The method according to claim 1, wherein the plant is a *Brassica juncea*.

4. The method according to claim 1, wherein the trace element is lead.

5. The method according to claim 1, wherein the trace element is selected from the group consisting of chromium, molybdenum and tungsten.

6. The method according to claim 1, wherein the trace element is selected from the group consisting of cadmium and mercury.

7. The method according to claim 1, wherein the trace element is selected from the group consisting of tellurium and polonium.

8. The method according to claim 1, wherein the trace element is uranium.

9. The method according to claim 1, wherein the enhanced accumulation is at least 50% greater than an otherwise comparable untransformed plant.

10. The method according to claim 1, wherein the medium is soil.

11. The method according to claim 1, wherein the nucleic acid is operably linked to a heterologous promoter, the plant is a *Brassica juncea*, and wherein the trace element is lead and the enhanced accumulation is at least 50% greater than an otherwise comparable untransformed plant.

12. The method according to claim 1, wherein the nucleic acid is operably linked to a heterologous promoter, the plant is a *Brassica juncea*, and wherein the trace element is selected from the group consisting of chromium, molybdenum and tungsten and the enhanced accumulation is at least 50% greater than an otherwise comparable untransformed plant.

13. The method according to claim 1, wherein the nucleic acid is operably linked to a heterologous promoter, the plant is a *Brassica juncea*, and wherein the trace element is selected from the group consisting of cadmium and mercury and the enhanced accumulation is at least 50% greater than an otherwise comparable untransformed plant.

14. The method according to claim 1, wherein the nucleic acid is operably linked to a heterologous promoter, the plant is a *Brassica juncea*, and wherein the trace element is uranium and the enhanced accumulation is at least 50% greater than an otherwise comparable untransformed plant.

15. The method according to claim 1, wherein the transformed plant is otherwise phenotypically the same as a corresponding untransformed plant.

16. The method according to claim 3, wherein the transformed plant is otherwise phenotypically the same as a corresponding untransformed plant.

17. The method according to claim 12, wherein the transformed plant is otherwise phenotypically the same as a corresponding untransformed plant.

18. The method according to claim 12, wherein the transformed plant is otherwise phenotypically the same as a corresponding untransformed plant.

19. The method according to claim 14, wherein the transformed plant is otherwise phenotypically the same as a corresponding untransformed plant.

* * * * *

UNITED STATES PATENT AND TRADEMARK OFFICE
CERTIFICATE OF CORRECTION

PATENT NO. : 6,974,896 B1
APPLICATION NO. : 09/365348
DATED : December 13, 2005
INVENTOR(S) : Terry et al.

It is certified that error appears in the above-identified patent and that said Letters Patent is hereby corrected as shown below:

On the title page,
Item [*] delete "0" and insert --367--.

Signed and Sealed this

Twenty-fifth Day of July, 2006

JON W. DUDAS
*Director of the United States Patent and Trademark Office*